Figure 1:
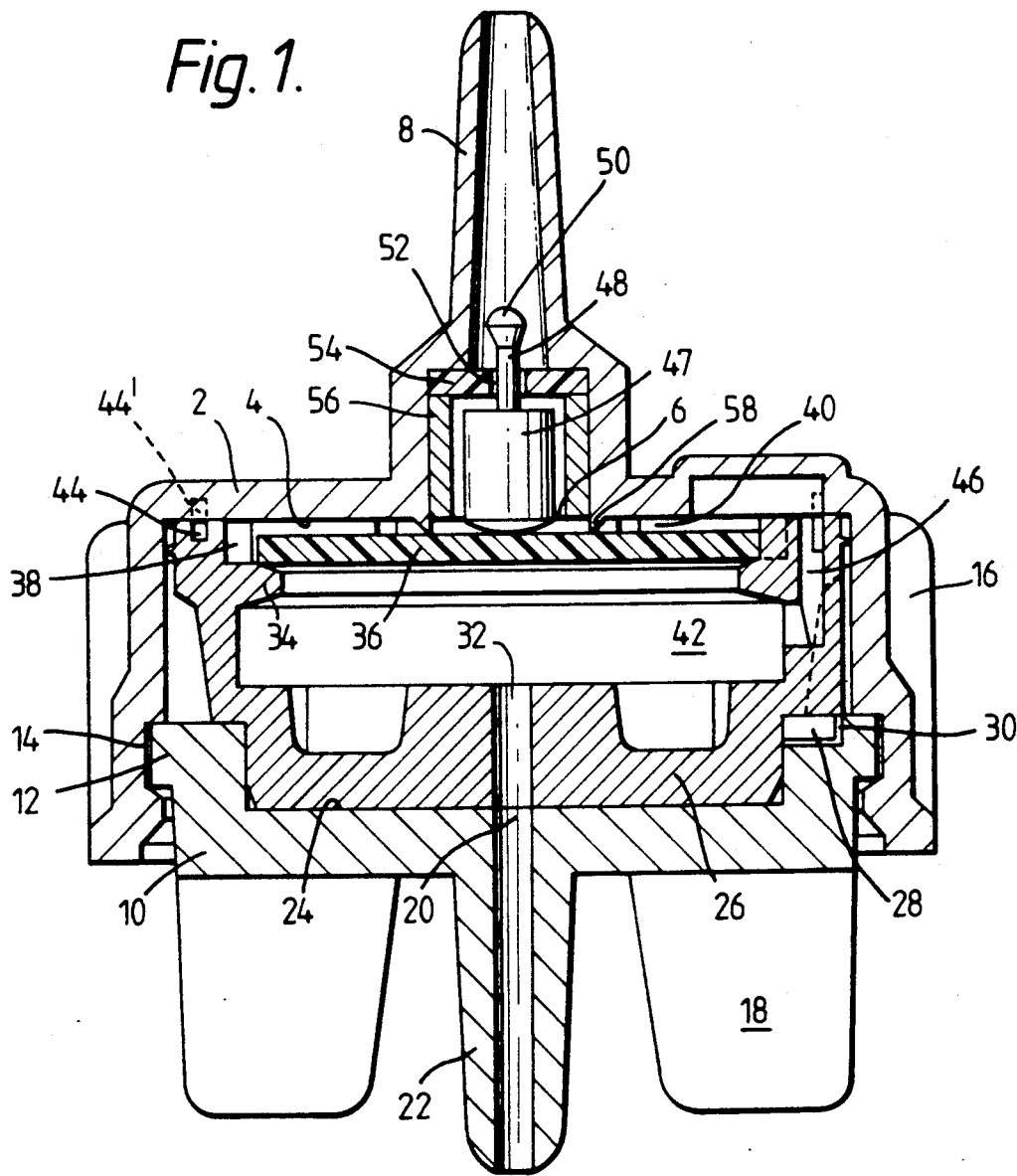

United States Patent [19]

Bron

[11] Patent Number: 5,137,522

[45] Date of Patent: Aug. 11, 1992

[54] PRESSURE-COMPENSATED INFUSION REGULATOR

[76] Inventor: Dan Bron, 36 Palmach Street, Haifa, Israel

[21] Appl. No.: 755,806

[22] Filed: Sep. 6, 1991

[30] Foreign Application Priority Data

Sep. 12, 1990 [IL] Israel .................................... 95660

[51] Int. Cl.$^5$ .............................................. A61M 5/00
[52] U.S. Cl. ......................................... 604/247; 604/9; 604/118; 137/501
[58] Field of Search .................... 604/247, 246, 9, 251, 604/86, 118; 137/501, 504, 843

[56] References Cited

U.S. PATENT DOCUMENTS

| | | |
|---|---|---|
| 3,782,858 | 1/1974 | Deters . |
| 4,000,740 | 1/1977 | Mittleman .......................... 604/86 |
| 4,343,305 | 8/1982 | Bron . |
| 4,796,660 | 1/1989 | Bron . |
| 4,867,198 | 9/1989 | Faust . |
| 4,904,236 | 2/1990 | Redmond et al. .............. 604/247 X |
| 5,009,391 | 4/1991 | Steigerwald ........................ 604/247 |
| 5,070,905 | 12/1991 | Paradis .............................. 604/86 X |

Primary Examiner—John D. Yasko
Attorney, Agent, or Firm—Larson and Taylor

[57] ABSTRACT

A dual-diaphragm, adjustable-rate, pressure-compensated infusion regulator includes a housing having inlet and outlet ports and an intermediate member, and a flexible main diaphragm retained along a peripheral portion thereof in the intermediate member. The regulator further includes a flow-regulating valve consisting of a valve head accessible to a high-pressure source and a valve stem which is attached to the valve head, and a flow-attenuating element of adjustable attenuating effect. A flexible auxiliary diaphragm is retained along a peripheral portion thereof in a high-pressure region and incorporates a valve seat for the valve head, the valve seat and the valve head defining between them a gap through which the liquid passes on its way from the high-pressure source into the inlet chamber.

14 Claims, 2 Drawing Sheets

PRESSURE-COMPENSATED INFUSION REGULATOR

The present invention relates to a pressure-compensated infusion regulator, and in particular to an adjustable-rate, dual-diaphragm pressure-compensated infusion regulator.

U.S. Pat. No. 4,796,660 discloses an infusion set in which a degree of output constancy was achieved by flow regulation at the inlet part of the regulator rather than at the outlet part as was common usage previously (see, for instance, U.S. Pat. No. 4,343,305). This was done by providing, in the high-pressure part of the regulator, a valve linked to, and following the movements of, the regulator diaphragm, and a valve seat fixedly located below the head of that valve. The infusion liquid passed through, and was throttled by, the annular gap between seat and head, which gap varied as a function of the pressure drop across the diaphragm.

While this arrangement wa definitely superior to conventional infusion sets inasmuch as the dripping-rate vs. time curve was flatter and smoother, and the clogging frequency of the flow attenuating groove was greatly reduced due to the filtering effect of the narrow gap, "fade-outs" or decay of output were experienced in dependence on pressure increase caused, e.g., by an increase in the difference of height between the infusion-liquid container and the patient. As a result, the valve head, exposed to full system pressure, produces a downward-directed force component acting on the diaphragm, which component is proportional to the full system pressure and varies with the latter. With the rise of pressure in the system, this extraneous force increases and pushes the diaphragm downwards, thereby obviously increasing the throttling action at the valve seat and affecting the output accordingly.

It is one of the objects of the present invention to overcome the drawbacks of the prior art infusion sets and to provide an infusion regulator with a constant, non-decaying output also at higher pressures.

According to the invention, this is achieved by providing a dual-diaphragm, adjustable rate, pressure-compensated infusion regulator, comprising an inverted-cup-shaped, first housing part having substantially cylindrical walls and a downward-facing bottom surface with an inlet port, said first housing part being provided with an inlet connector connectable to a relatively high-pressure infusion-liquid source; a second housing part attachable to said first housing part and having an outlet port; an intermediate member comprised at least of an annular portion interposed between and rotatable relative to either of said first and said second housing parts, and having means rendering it stationary relative to the other one of said housing parts; a flexible main diaphragm retained along a peripheral portion thereof in said intermediate member and defining with its upper surface an inlet chamber and with its lower surface, an outlet chamber; a flow-regulating valve comprised of a valve head accessible to said high-pressure source and a valve stem one end of which is attached to said valve head; a flow-attenuating element of adjustable attenuating effect disposed in the path of said liquid from said inlet chamber into said outlet chamber; a flexible auxiliary diaphragm retained along a peripheral portion thereof in a high-pressure region upstream of said inlet chamber and incorporating a valve seat for said valve head, said valve seat and said valve head defining between them a gap through which the liquid passes on its way from said high-pressure source into said inlet chamber, said valve head being adapted to be acted upon by a first force tending to reduce said gap, and by a second force tending to increase said gap, a state of equilibrium between said forces defining the set point of said pressure-compensated infusion set; wherein said force, by acting upon said flexible auxiliary diaphragm and flexing same in direction towards said main diaphragm, enhances the effect of said second force.

The invention will now be described in connection with certain preferred embodiments with reference to the following illustrative figures so that it may be more fully understood.

With specific reference now to the figures in detail, it is stressed that the particulars shown are by way of example and for purposes of illustrative discussion of the preferred embodiments of the present invention only and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Figure 2:
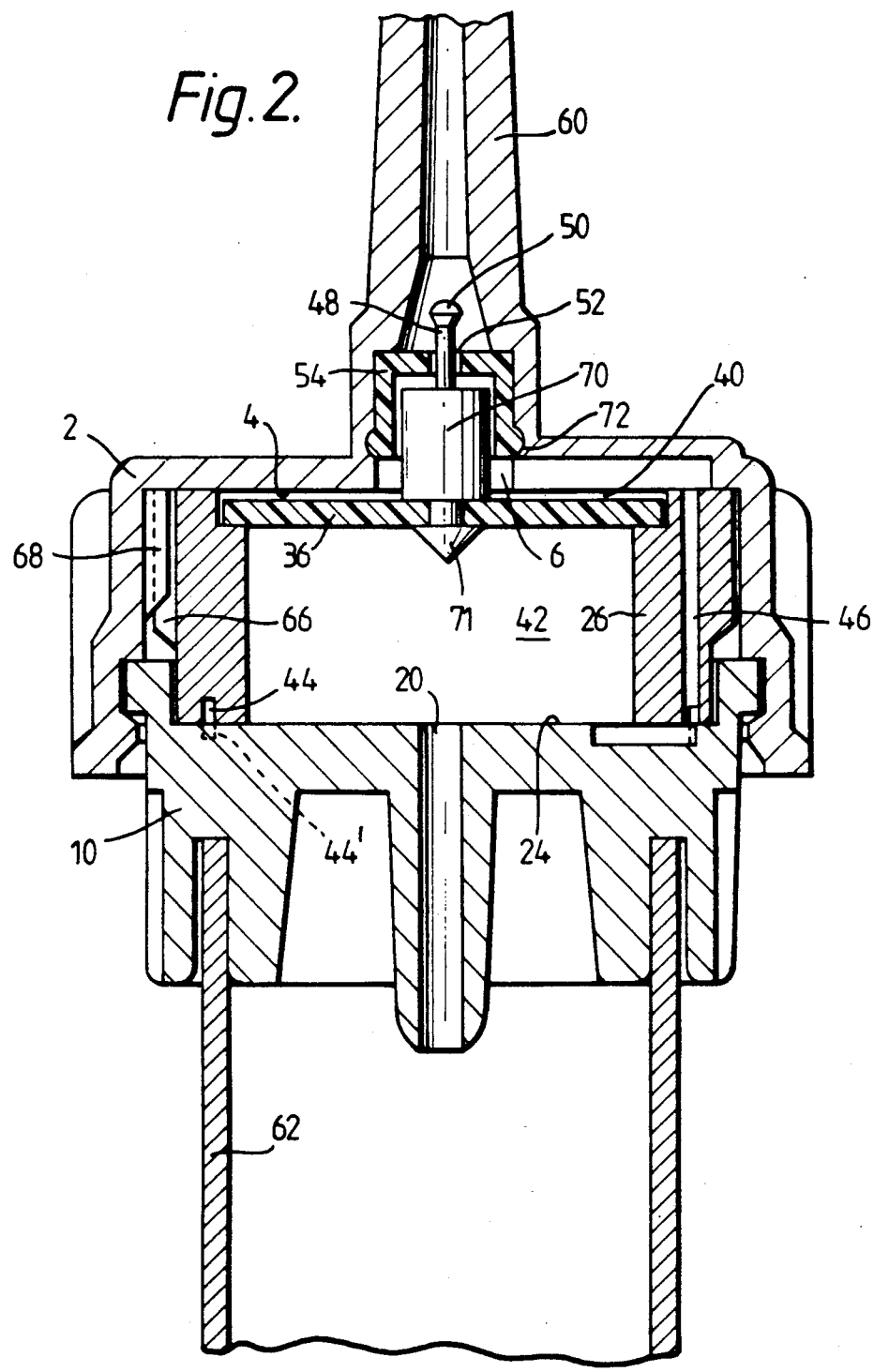

In the drawings:

FIG. 1 is a cross-sectional view of a first embodiment of the infusion regulator according to the invention; and FIG. 2 is a similar view of a second embodiment thereof.

Referring now to the drawings, there is seen in FIG. 1 an in-line infusion regulator comprising a first housing part in the shape of an inverted cup of substantially cylindrical walls and a downward-facing bottom surface 4 with an inlet port 6. An inlet connector 8 permits connection to tubing.

A second housing part 10 snap-fits with its peripheral rim 12 into a groove 14 in the first housing part 2 and, with respect to the latter, has thus one degree of freedom in rotation. Relative mutual rotation of the two housing parts 2 and 10 (for a purpose to be discussed further below) is facilitated by a plurality of ribs 16 on the outer surface of the first housing part 2 on one hand, and two wing-like projections 18 integral with the second housing part 10, on the other. The latter is also provided with an outlet port 20 and an outlet connector 22.

Between the bottom surface 4 of the first housing part 2 and the major top surface 24 of the second housing part 10, and contacting both, there is mounted the intermediate member 26 which, due to a number of lugs 28 engaging, in assembly, a corresponding number of appropriately shaped recesses 30 in the second housing part 10, can only rotate together with the latter. A bore 32 in the lower part of the member 26 is aligned with the outlet port 20 of the second housing member 10.

In the upper portion of the member 26 there is seen an inward-projecting peripheral rim 34 on which is freely seated the flexible, elastically-deformable main diaphragm 36, centered by means of a plurality of ribs 38. The diaphragm 36 defines, with its upper surface, an inlet chamber 40 and with its lower surface, an outlet chamber 42.

Also seen is the flow-attenuating groove 44 and the duct 46 connecting the inlet chamber 40 via the active portion of the groove 44 with the outlet chamber 42.

Freely seated on the diaphragm 36 is a valve-controlling pad 47 attached to, or integral with, a valve stem 48 that carries the valve head 50. There is also seen a valve seat 52 which, together with the valve head 50, defines a gap through which the infusion liquid can reach the inlet chamber 40.

So far the embodiment shown in FIG. 1 is similar to the design of the infusion regulator shown in FIG. 7 of the above-mentioned U.S. Pat. No. 4,796,660, which also explains in detail the manner in which the constant-output (i.e., flow-regulation) feature operates, while the adjustable-rate feature is exhaustively explained in U.S. Pat. No. 4,343,305.

The advantage of the present infusion regulator resides in the manner in which it solves the above-mentioned problem of output decay at relatively high pressures, when the diaphragm, as mentioned earlier, is liable to overreact, i.e., to bulge to a degree that, in the infusion set of U.S. Pat. No. 4,796,660, would cause the valve head to throttle the flow of infusion fluid almost to zero.

In the embodiment of FIG. 1 of the present invention, the valve seat 52 is not a hole in a rigid portion of the first housing part 2, but in a flexible, discoid auxiliary diaphragm 54 retained in housing part 2 by means of a sleeve 56 and exposed to the high pressure of the infusion liquid source, which pressure, when rising, deflects the auxiliary diaphragm 54. It will be appreciated that while the deflection of the main diaphragm under pressure, i.e., it bulging downwards, causes the gap between valve head 50 and valve seat 52 to be reduced, deflection of the auxiliary diaphragm 54 has the opposite effect of enlarging the gap. Obviously, the respective parameters of the two diaphragms (material, thickness, active diameter) will be selected in such a way that the corrective deflection of the auxiliary diaphragm 54 has the required compensatory effect.

There is also seen a circular, knife-edge-like rim 58 projecting from the bottom surface 4 of the first housing part 2, which about touches the main diaphragm 36 in the relaxed state thereof. The rim 58 constitutes the seat of the main diaphragm when serving, as it does, as non-return valve.

It should be noted that the flow-attenuating groove 44 could also be provided in the bottom surface 4 of the first housing part 2 rather than in the intermediate member 26, as indicated by the dashed groove 44'.

The embodiment shown in FIG. 2 differs in several details from that of FIG. 1.

Instead of the tube connector 8, there is provided a pointed snout 60 adapted to be pushed into the infusion bag. To the second housing part 10 is attached a transparent drip chamber 62 permitting visual monitoring of the functioning of the regulator. The intermediate member 26 is annular rather than cup-shaped and the flow-attenuating groove 44 is provided in the lower edge of the member 26. It could also be located on the surface 24 of the second housing part 10, as indicated by the dashed groove 44'.

Due to the location of the groove 44 at the interface: intermediate member 26/second housing part 10, the intermediate member 26 must obviously be stationary relative to the first housing part 2. This is achieved by providing slots 66 on the periphery of the intermediate member 26, in which engage ribs 68 of appropriate size and spacing.

A linking rod 70 firmly connects the valve stem 48 and valve head 50 to the main diaphragm 36, by means of a barb fastener 71, and the auxiliary diaphragm 54 is now in the shape of an inverted cup having a beaded edge 72 retained in an undercut in the cylindrical bore constituting the inlet port 6.

The embodiment of FIG. 2 has no use for a non-return valve because of the need, during the priming stage of the regulator, to release air upwardly.

While the preferred embodiments of the present invention are provided with the above-mentioned adjustable-rate feature, it will be appreciated that the novel feature of the present invention, i.e., the non-decaying output also at higher pressures is applicable also to non-adjustable infusion regulators.

It will be evident to those skilled in the art that the invention is not limited to the details of the foregoing illustrated embodiments and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A dual-diaphragm, adjustable-rate, pressure-compensated infusion regulator, comprising:

an inverted-cup-shaped first housing part having substantially cylindrical walls and a downward-facing bottom surface with an inlet port, said first housing part being provided with an inlet connector connectable to a relatively high-pressure infusion-liquid source;

a second housing part attachable to said first housing part and having an outlet port;

an intermediate member comprised at least of an annular portion interposed between and rotatable relative to either of said first and said second housing parts, and having means rendering it stationary relative to the other one of said housing parts;

a flexible main diaphragm retained along a peripheral portion thereof in said intermediate member and defining with its upper surface an inlet chamber and with its lower surface, an outlet chamber;

a flow-regulating valve comprised of a valve head accessible to said high-pressure source and a valve stem one end of which is attached to said valve head;

a flow-attenuating element of adjustable attenuating effect disposed in the path of said liquid from said inlet chamber into said outlet chamber;

a flexible auxiliary diaphragm retained along a peripheral portion thereof in a high-pressure region upstream of said inlet chamber and incorporating a valve seat for said valve head, said valve seat and said valve head defining between them a gap through which the liquid passes on its way from said high-pressure source into said inlet chamber, said valve head being adapted to be acted upon by a first force tending to reduce said gap, and by a second force tending to increase said gap, a state of equilibrium between said forces defining the set point of said pressure-compensated infusion regulator;

wherein said force, by acting upon said flexible auxiliary diaphragm and flexing same in a direction towards said main diaphragm, enhances the effect of said second force.

2. The infusion regulator as claimed in claim 1, wherein said auxiliary diaphragm is discoid and is retained in said high-pressure region by a retaining sleeve.

3. The infusion regulator as claimed in claim 1, wherein said auxiliary diaphragm is in the shape of an inverted cup having a beaded edge retained in an undercut in said first housing part.

4. The infusion regulator as claimed in claim 1, further comprising a contact pad attached to the free end of said valve stem and adapted to be pushed by said main diaphragm.

5. The infusion regulator as claimed in claim 1, further comprising a linking rod attached at one of its ends to the free end of said valve stem and at the other one of its ends to said main diaphragm.

6. The infusion regulator as claimed in claim 1, wherein said flow-attenuating element is an arcuate groove the flow-attenuating effect of which can be adjusted by rotary displacement of one of said housing parts relative to the other one.

7. The infusion regulator as claimed in claim 1, further comprising a circular rim projecting from the bottom surface of said first housing part and facing said main diaphragm, said rim serving as the seat of said main diaphragm when acting as non-return valve.

8. The infusion regulator as claimed in claim 1, wherein at least one of said first and second housing parts is provided with connection means for connecting same to tubing.

9. The infusion set as claimed in claim 1, wherein said second housing part is provided with means for attachment of an at least partly transparent drip chamber.

10. The infusion regulator as claimed in claim 1, wherein said first housing part is provided with a snout for introducing at least its upper end into an infusion-liquid container.

11. The infusion regulator as claimed in claim 1, wherein said flow-attenuating element is located on the upper rim of said intermediate member.

12. The infusion regulator as claimed in claim 1, wherein said flow-attenuating element is located on the bottom surface of said first housing member.

13. The infusion regulator as claimed in claim 1, wherein said flow-attenuating element is located on the lower rim of said intermediate member.

14. The infusion regulator as claimed in claim 1, wherein said flow-attenuating element is located on the upper surface of said second housing member.

* * * * *